(12) United States Patent
Stivers (10) Patent No.: US 8,475,394 B1
(45) Date of Patent: Jul. 2, 2013

(54) PET DNA SPECIMEN SAMPLING FOR TRANSPORT AND LONG TERM STORAGE

(76) Inventor: John Elliot Randal Stivers, Atlanta, GA (US)

( * ) Notice: Subject to any disclaimer, the term of this patent is extended or adjusted under 35 U.S.C. 154(b) by 418 days.

(21) Appl. No.: 12/803,342

(22) Filed: Jun. 24, 2010

(51) Int. Cl.
*A61B 10/00* (2006.01)

(52) U.S. Cl.
USPC .......................................... 600/572; 600/562

(58) Field of Classification Search
USPC ........... 600/572, 569, 562, 570, 571; 606/133
See application file for complete search history.

(56) References Cited

U.S. PATENT DOCUMENTS

| | | | | |
|---|---|---|---|---|
| 3,712,296 | A * | 1/1973 | Gradone | 600/572 |
| 3,954,563 | A * | 5/1976 | Mennen | 600/572 |
| 4,175,008 | A * | 11/1979 | White | 600/572 |
| 4,593,694 | A * | 6/1986 | Langenbach, Jr. | 606/133 |
| 5,096,062 | A * | 3/1992 | Burkardt et al. | 206/361 |
| 5,664,579 | A * | 9/1997 | Caillouette | 600/572 |
| 6,620,158 | B2 * | 9/2003 | Ronci | 606/36 |
| 7,850,922 | B2 * | 12/2010 | Gallagher et al. | 422/501 |
| 7,998,680 | B2 * | 8/2011 | Thomas et al. | 435/6.1 |
| 2005/0010132 | A1 * | 1/2005 | Pestes et al. | 600/572 |
| 2005/0010133 | A1 * | 1/2005 | Pestes et al. | 600/572 |
| 2005/0169800 | A1 * | 8/2005 | Bianca | 422/61 |
| 2006/0074347 | A1 * | 4/2006 | Eguchi et al. | 600/573 |
| 2007/0128612 | A1 * | 6/2007 | Povlich | 435/6 |
| 2007/0208274 | A1 * | 9/2007 | Ostrowski et al. | 600/573 |
| 2007/0255175 | A1 * | 11/2007 | Sangha | 600/572 |
| 2007/0299364 | A1 * | 12/2007 | Sangha | 600/572 |
| 2008/0300505 | A1 * | 12/2008 | Oommen | 600/562 |
| 2010/0274155 | A1 * | 10/2010 | Battrell et al. | 600/572 |
| 2011/0004122 | A1 * | 1/2011 | Sangha | 600/572 |
| 2011/0087133 | A1 * | 4/2011 | Ching et al. | 600/572 |
| 2011/0144534 | A1 * | 6/2011 | Gombrich | 600/572 |

FOREIGN PATENT DOCUMENTS

WO WO 2005079871 A1 * 9/2005

* cited by examiner

*Primary Examiner* — Jeffrey G Hoekstra
*Assistant Examiner* — May Abouelela
(74) *Attorney, Agent, or Firm* — Robert Z. Evora, Esq.

(57) ABSTRACT

A kit and method for collecting, storing and transporting genetic samples from an animal to a storage facility. The kit comprises at least a collection swab, a protective tube, a follicle sample collection card, and an extraction device. The collection swab is housed within a sterile protective package. The collection swab has a shaft connected at one end by a collection head. The collection swab includes a cap and plug, wherein the cap is encircled around the shaft of the collection swab. The protective tube is adapted to receive the collection head of the collection swab. The follicle sample collection card has a protective backing covering an adhesive strip disposed on the follicle sample collection card. The extraction device is provided to pull at least one hair with follicle from the animal. The kit may also include a specimen storage enrollment card to record pertinent information, and an envelope may be provided for storage and delivery of the protective tube and the follicle sample collection card including the respective genetic samples to a storage facility for processing and storage of the genetic samples at a controlled temperature above freezing.

16 Claims, 6 Drawing Sheets

PET DNA SPECIMEN SAMPLING FOR TRANSPORT AND LONG TERM STORAGE

BACKGROUND

1. Field of the Invention

This invention generally relates to a kit for sampling and storing cellular specimens and the method of preservation during transport, and in particular to a kit for collecting and delivering Deoxyribonucleic Acid (DNA) samples of a domestic pet to a storage facility which stores the DNA samples at a controlled temperature above freezing for extended periods of time.

2. Description of the Related Art

Although embroiled in much debate, as modern scientific advances evolve in our society, so too do the advances in genetic replication. The successful molecular and cellular replication of a human genome has peaked much interest and its useful technological advances in the treatment of various disease conditions. The same holds true for any type of animal including a beloved pet.

Every living thing is made up of DNA. A pet's DNA now holds the key to their sustained health and future. While cloning is still beyond the reach of most people financially, every year the costs fall, and some day in the near future pet owners will inexpensively be able to use the DNA of their beloved animal companions to consider bringing them back after a loss or accident.

The productivity of DNA sequencing technologies has increased more than 20,000-fold over the past 15 years. At this rate of improvement, productivity has doubled approximately every twelve months or improved by nearly six percent per month. Over the same time period, costs of sequencing have fallen 10,000-fold, halving approximately every 13 months. At the same time, the accuracy of gene synthesis technologies has improved significantly. Unfortunately, therapies of this type are by and large still in the early stages of development and it may well be many years before they are readily accessible.

In the future, a pet's stored DNA could also be used to clone its organs. If a pet should require a lifesaving organ transplant, an organ harvested from that pet's own DNA could potentially assist in making a transplant with a cloned organ a very high likelihood that it will not be rejected.

Since it is understood that cells harvested from an aging animal are less robust than those from an animal younger in age, there is motivation to provide collect and store youthful genes for future use. The idea being that cells harvested from an animal relatively early in life can be revived for use in the same animal for genetic replication or cellular based therapy.

Thus, it would be particularly useful to provide an easy to use method and kit that can be carried out by an individual without any specialized training, who can collect a viable, sterile sample of suitable cells for preservation and future use.

SUMMARY

The present invention includes a kit for collecting, storing and transporting genetic samples. The kit comprises a collection swab, a protective tube, a follicle sample collection card, and an extraction device. The collection swab is housed within a sterile protective package. The collection swab has a shaft connected at one end by a collection head. The collection swab further includes a cap and plug, wherein the cap is encircled around the shaft of the collection swab. The protective tube is adapted to receive the collection head of the collection swab. The follicle sample collection card has a protective backing covering an adhesive strip disposed on the follicle sample collection card. The extraction device is provided to pull at least one hair with follicle from the animal.

The kit may also include a specimen storage enrollment card to record pertinent information. An envelope may be provided for storage and delivery of the protective tube and the follicle sample collection card including the respective genetic samples to a storage facility for processing and storage.

In another embodiment, a method is provided for collecting, and storing genetic samples. The method comprises pulling a cap encircling a shaft of a collection swab back away from within a protective tube to remove a collection head from within a sterile compartment within the protective tube. The collection head is scraped against an inner cheek of the mouth of an animal to receive a first specimen sample. The shaft is securely inserted back into an open end of the protective tube until a flanged top portion of the cap seats flush with the open end of the protective tube. The shaft of the collection swab is then pulled back out of the center of the cap until the collection head is completely disengaged from a second end of the shaft, and the center of the cap is plugged with a plug.

At least one hair is pulled with a follicle from the animal. A protective backing is removed from an adhesive strip disposed on the follicle sample collection card. The at least one hair pulled is aligned onto the adhesive strip so that the follicle is positioned to one side of the adhesive strip. The follicle sample collection card is then closed at a seam over the hair and follicle for storage.

These and other objects, features, and/or advantages may accrue from various aspects of embodiments of the present invention, as described in more detail below.

BRIEF DESCRIPTION OF THE DRAWINGS

Various exemplary embodiments of this invention will be described in detail, wherein like reference numerals refer to identical or similar components or steps, with reference to the following figures, wherein.

DETAILED DESCRIPTION

Particular embodiments of the present invention will now be described in greater detail with reference to the figures. Below illustrates a method, apparatus and kit for obtaining a genetic specimen sample and storing the genetic specimen sample, and method for transport and long term preservation of the genetic specimen sample.

In particular, the DNA sampling kit is for the personal use of obtaining various types DNA samples from an animal. The kit is simple to use and adapted for use by a non-professional individual to obtain an animal cell specimen sample. The need for the individual to travel to a processing facility or to solicit the services of a professional for obtaining the sample is eliminated. The kit includes a process for collecting various genetic samples, storage devices and for transport of the genetic animal cell specimen sample. The genetic specimen sample is provided with packaging and shipping the genetic specimen sample to a storage facility for further processing, and storage preservation of the genetic specimen sample for future culturing and/or clonal expansion of the cells, DNA typing analysis, genetic manipulations, and the like.

Figure 1:
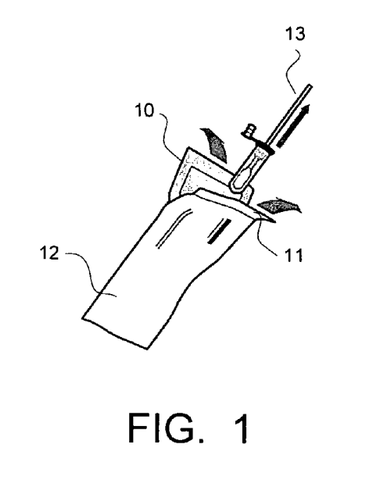
FIG. 1 illustrates peeling apart a package and removing a swab and protective cover.

FIG. 1 shows a protective package 12 being opened. The protective package 12 is peeled apart to access a collection swab 13. That is, a first portion 10 of the protective package 12 is peeled from a second portion 11 of the protective package 12 and the collection swab 13 is removed.

Figure 2:
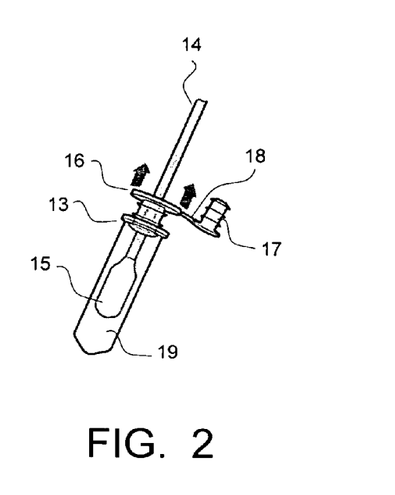
FIG. 2 shows grasping and pulling back a cap from a tube to remove the swab.

FIG. 2 illustrates the collection swab 13 in more detail. The collection swab 13 includes a shaft 14 connected to a collection head 15. A cap 16 is disposed around the shaft 14 and a plug 17 is tethered via a strap 18 to the cap 16. A protective tube 19 is shown disposed around the collection head 15 of the collection swab 13. As shown in operation in FIG. 2, the cap 16 and shaft 14 are grasped and pulled back from within the protective tube 19 to remove the collection head 15 from within a sterile compartment within the protective tube 19. It is to be understood that the collection swab may employ a variety of different constructions suitable to collect the specimen from the animal 20 that is commercially available and/or later discovered in accordance with this disclosure.

Figure 3:
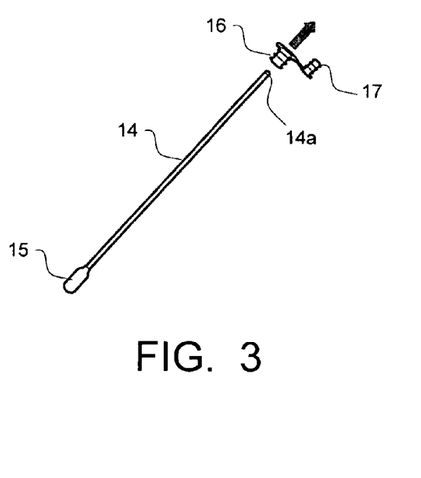
FIG. 3 depicts removing the cap from a shaft of the swab.

FIG. 3 depicts removing the cap 16 and the plug 17 from the shaft 14 of the collection swab 13 in order to maximize the useable of the length of the shaft 14 of the collection swab 13 and to maintain a firm grip of the shaft 14. The cap 16 and plug 17 are removed from the shaft 14 toward a first end 14a of the shaft in a direction away from the collection head 15 of the collection swab 13.

Figure 4:
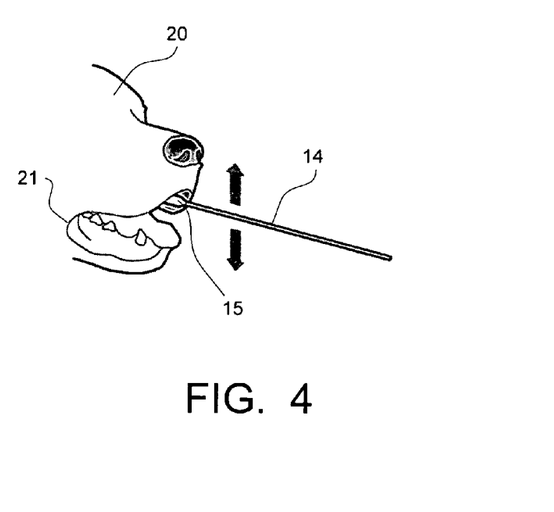
FIG. 4 illustrates brushing the swab against the inside of an animal for a predetermined period of time.

FIG. 4 illustrates brushing of the buccal (i.e., buccal meaning inner-cheek) collection head 15 of the swab 13 against the inner check 21 of the mouth of the animal 20 for a predetermined period of time. The swab 13 is gently rubbed against the inside of the cheek, and DNA from the mouth is collected. The predetermined period of time should be long enough to scrape a sufficient amount of a cellular specimen from the inner cheek 21 of the animal 20. A suitable predetermined period of time may be, for example, may be about a minute of scraping of the inner cheek 21 of the animal 20.

It is to be understood that the animal 20 may be any type of animal, including but not limited to, a domesticated pet, such as a family dog, cat, horse, and/or any other type of domestic pet within the scope of this invention. It is also to be understood that any type of DNA may be selected from various places on the body of the animal, such as via a biopsy, skin scrapings, blood, hair and/or any other method now known or later discovered suitable for recovering DNA in accordance with this concept.

Figure 5:
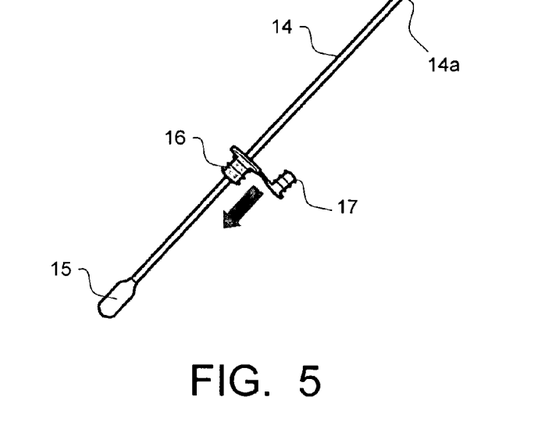
FIG. 5 shows replacing the cap over the shaft of the swab and placing the swab back into the tube.

FIG. 5 shows replacing the cap 16 and plug 17 back onto the shaft 14 over and from the first end 14a of the shaft 14, opposite the collection head 15 along the shaft 14. The cap 16 and plug 17 are slid back over the shaft 14 to an a predetermined position so that the collection head 15 may be disposed comfortably within the protective tube 19 as it is placed back into of the protective tube 19.

Figure 6:
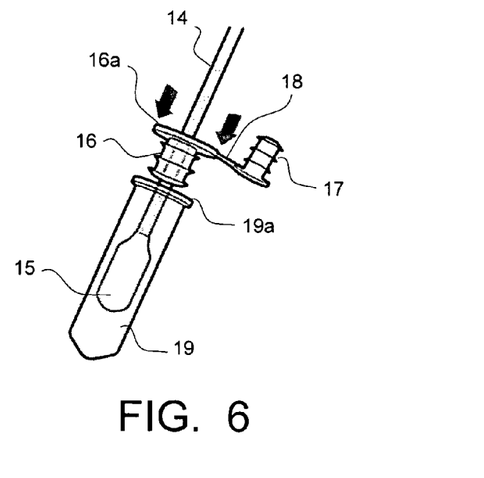
FIG. 6 depicts inserting the cap back securely into the tube until the top of the cap is flush with the top of the tube.

FIG. 6 depicts aligning and inserting the cap 16 back securely into an open end 19a of the protective tube 19 until a flanged top portion 16a of the cap 16 seats flush with the open end 19a of the protective tube 19. As shown, the cap 16 is pushed downward onto the open end 19a of the protective tube 19 until it sits flush with the flanged top portion 16a of the cap 16.

Figure 7:
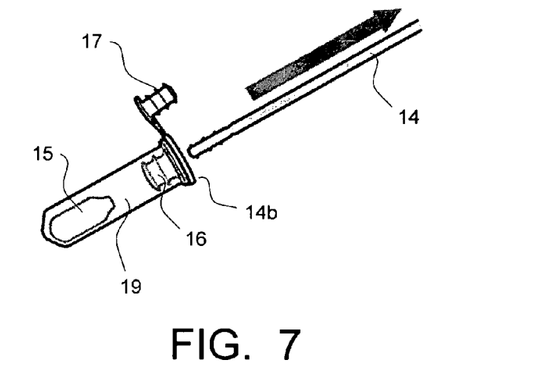
FIG. 7 illustrates pulling the shaft of the swab directly back out of the cap so that the swab is disengaged from the shaft.

FIG. 7 shows the shaft 14 of the collection swab 13 being pulled back out of the center of the cap 16, now seated within the protective tube 19, so that the collection head 15 of the swab 13 may be completely disengaged from a second end 14b of the shaft 14. Likewise, the shaft 14 is completely removed from the center of the cap 16 and from the protective tube 19.

Figure 8:
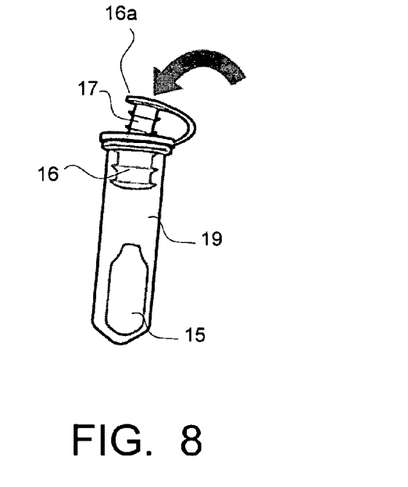
FIG. 8 shows plugging the top of the tube until the plug is flush with the cap.

FIG. 8 illustrates the plugging of the center of the cap 16 with the tethered plug 17. The outer diameter of the plug 17 is dimensioned to snugly fit within an inner diameter of the center of the cap 16 so that a tight seal may be formed when the plug 17 is secured flush within the center of the cap 16.

Figure 9:
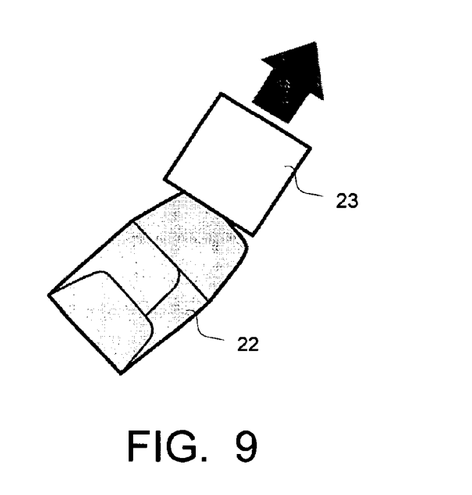
FIG. 9 depicts opening the follicle collection envelope and removing a sample billfold card.

In FIG. 9, a follicle sample collection card 23 is removed from an envelope 22. As shown, the follicle sample collection card 23 is a billfold configuration (as shown and described in more detail in FIG. 12). However it is to be understood that the follicle sample collection card 23 may take any suitable configuration.

Figure 10:
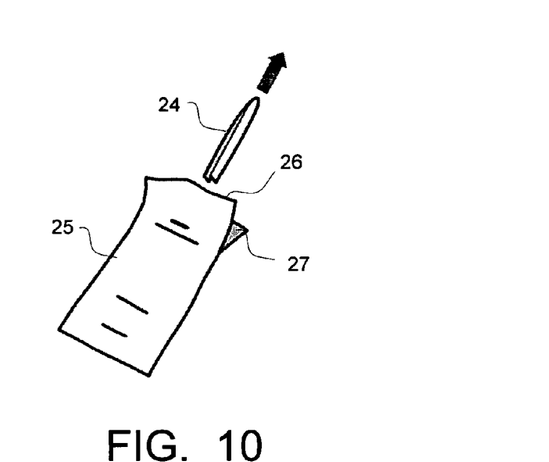
FIG. 10 illustrates removing the tweezers from a storage package by peeling apart the storage package at an end.

FIG. 10 illustrates removing tweezers 24 from a tweezers storage package 25. The tweezers 24 are removed by peeling apart a first end 26 from a second end 27 of the tweezers storage package 25. The object of enclosing the tweezers 24 is to provide a pre-use environment protected from contamination in the surrounding area.

Figure 11:
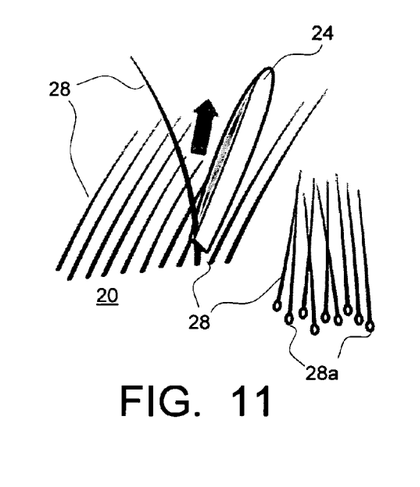
FIG. 11 shows the extraction of a predetermined number of hairs from the animal close to the base of the hair to extract the follicle.

In FIG. 11, a predetermined number of hairs 28 are shown being extracted from the animal 20 close to the base of the hair 28. The object is to extract the hair 28 and the follicle 28a together as a complete sample. One way to achieve this would be to pull the hairs 28 from as close to the follicle as possible in order to extract the follicle 28a as well the shaft of the hair 28.

Figure 12:
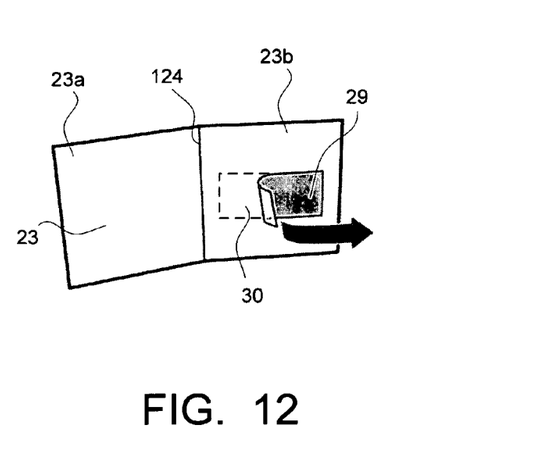
FIG. 12 depicts removing a protective backing from an adhesive strip on the sample billfold card.

FIG. 12 shows a protective backing 29 being removed from an adhesive strip 30 disposed on the follicle sample collection card 23. The follicle sample collection card 23 is configured as a billfold. The follicle sample collection card 23 includes a first panel 23a and a second panel 23b meeting at a folding seam 124.

The follicle sample collection card 23 is designed to preserve the genetic specimen over long periods of time. The properties of the exemplary follicle sample collection card 23 may be suitably selected from a variety of different materials in order to provide for long life preservation of the genetic specimen. The follicle sample collection card 23 may be composed of an acid free interior wrapping and/or a light shielding composition to prevent from degradation of the genetic specimen stored therein. The follicle sample collection card 23 may be made from a sturdy material capable of protecting the genetic sample during transport and storage thereof. Likewise, the envelope 22 may also be composed of a light shielding composition in order to prevent degradation of the genetic specimen from light exposure.

Figure 13:
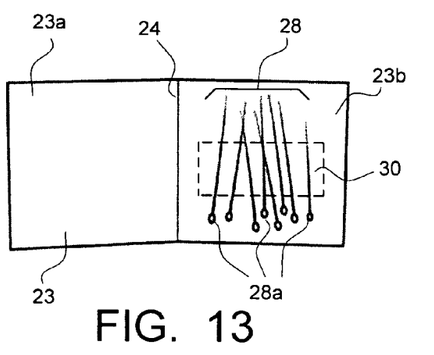
FIG. 13 demonstrates affixing the various hairs to the billfold card in a vertical orientation so that the follicles are positioned to one side of the protective backing.

FIG. 13 demonstrates the use of the follicle sample collection card 23. As shown, the various hairs extracted from the animal 20 are substantially oriented onto the adhesive strip 30. The goal is to affix the various hairs 28 to adhesive strip 30 of the follicle sample collection card 23 in ari orientation so that the generic rich follicles 28a are positioned to one side of the adhesive strip 30. This configuration provides sufficient protection to the hairs 28 and the hair follicles 28a during storage and transport of the hair 28 samples. Proper alignment onto the adhesive strip 30 will allow the hairs 28 and the hair follicles 28a to stay positioned within, and to maintain contact with the acid free follicle sample collection card 23.

Figure 14:
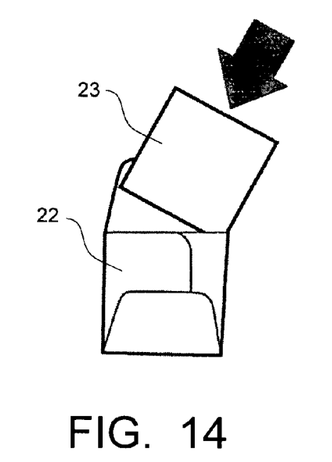
FIG. 14 illustrates placing the sample card securely back into the envelope.

In FIG. 14, the follicle sample collection card 23 is closed at the seam 24 and placed securely back into the envelope 22. The unique construction of the follicle sample collection card 23 is such that the hair 28 samples and follicles 28a are protected and preserved within the follicle sample collection card 23.

Figure 15:
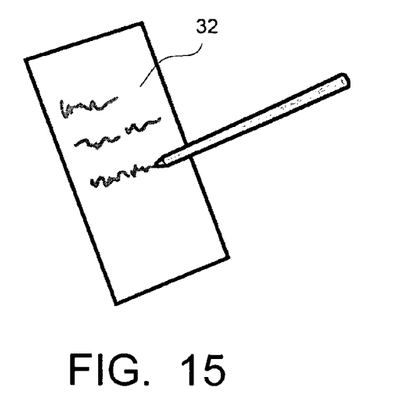
FIG. 15 depicts filling out a specimen storage enrollment card.

FIG. 15 depicts filling out a specimen storage enrollment card 32 with pertinent identification information about the sample and the person preserving the specimen sample.

Figure 16:
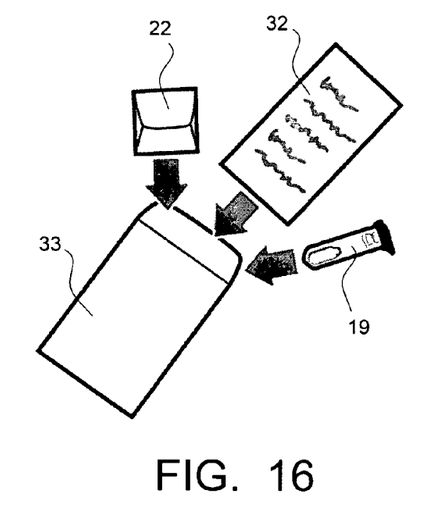
FIG. 16 shows placing the tube with the swab head, the sample billfold card with the hair samples, and the specimen storage enrollment card into a postage paid return envelope.

FIG. 16 shows the placing of the various items into a return envelope 33 for storage and/or mailing. The protective tube 19 along with the sealed and secured swab head 15, the follicle sample collection card 23 with the hair samples 28, and the specimen storage enrollment card 32 is placed into the larger return envelope 33.

Figure 17:
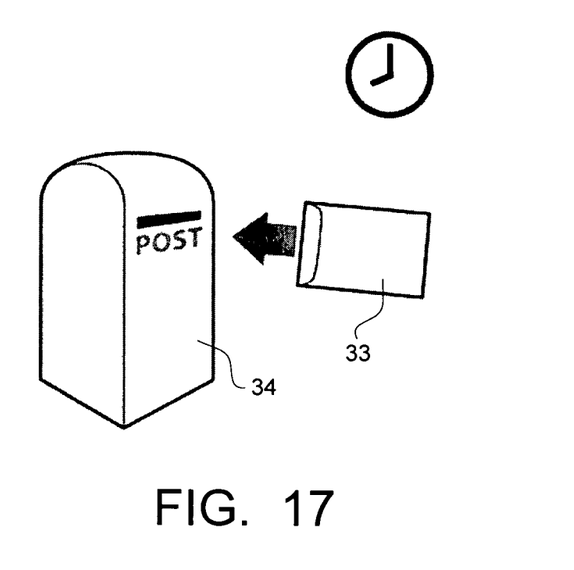
FIG. 17 shows placing the return envelope in the mail within a predetermined time period from extraction of the specimen samples to ensure maximum DNA integrity.

FIG. 17 illustrates the placing of the larger return envelope 33 within a predetermined time period after the extraction of the hair 28 and buccal cell specimen (from the inner cheek) on the collection head 15. Ideally, the various samples will be returned in the larger return envelope 33 by post office 34 immediately to a storage facility (i.e., the facility may be a storage facility, and/or a laboratory, or various other suitable locations for storage, use and the like) to ensure maximum DNA integrity of the various samples.

Once the genetic specimens are received at a storage facility (laboratory or the like), the buccal cells are made ready for transfer from the collection head 15 of the swab 13 onto a safe, secure and reliable medium for storage. Any storage medium may be designed and/or used for the collection and control temperature storage above freezing of the biological samples for subsequent DNA analysis and use. That is, rapid isolation of pure DNA is achieved when the buccal cells are lysed and high molecular weight DNA (e.g., nucleic acids) are immobilized and stabilized within the storage medium's matrix. The process is designed to kill pathogens and prevent future colonization by bacteria, fungi or other microorganisms, and protects the DNA from microbial and environmental degradation. Genomic DNA stored on various mediums may be stored at a controlled temperature above freezing for a number of years (and/or any suitable length of time, such as from as wide time range, e.g., one day to a number of decades, to a smaller window of time, e.g., from weeks to 20 years) without exhibiting any loss in genetic efficiency. Since the genetic material has sufficiently dried prior to arrival at the storage facility, a purified liquid or moistener, such as distilled, purified water or the like may be applied to the collection head 15 in order to transfer the buccal cells from the collection head to the storage medium. Various types of storage mediums (e.g., but not limited to, a pretreated card, a gel/solid based capsule, inert gas sealed container and/or the like), now known or later discovered suitable for this application, are contemplated in accordance with the kit, systems and methods of this invention.

The storage facility may be provided at a control temperature above freezing and/or any suitable climate and humidity controlled environment in which the genetic specimen will be archived and preserved for sufficiently long periods of time. In this way, the potential for cross-contamination between samples is reduced and/or shear forces associated with conventional extraction methods is eliminated.

Figure 18:
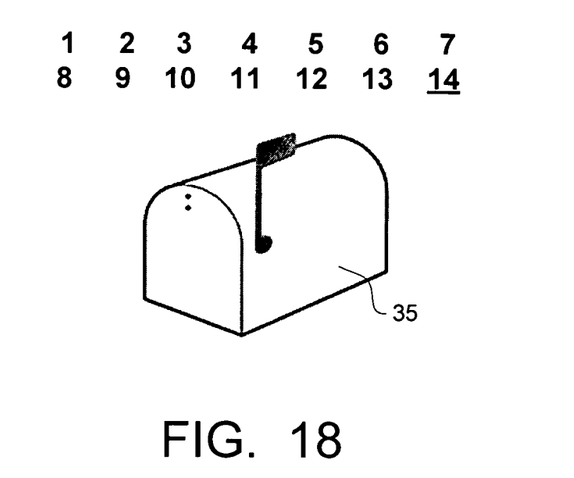
FIG. 18 illustrates receipt of acknowledgment of receipt of the specimen sample within a predetermined period of time after receipt and processing by a storage facility.

FIG. 18 depicts the acknowledgment of receipt of the specimen by mailbox 35 samples within another predetermined period of time after receipt and processing by the storage facility. Various times for receipt of acknowledgment are possible, for example 14 days after mailing of the sample in the return envelope 33.

Figure 19:
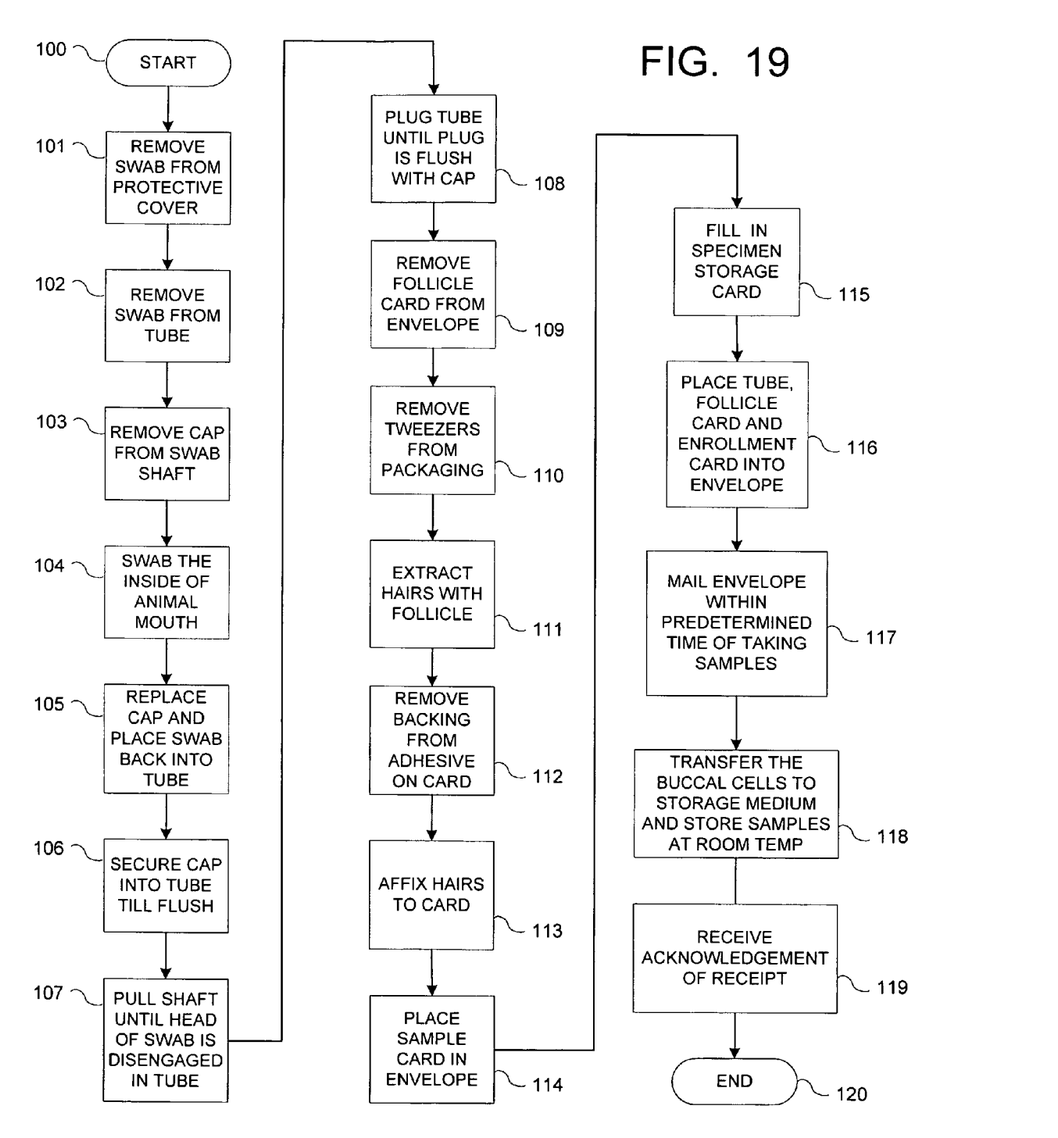
FIG. 19 illustrates a method for obtaining a specimen sample and storing the specimen sample, and method for transport and preservation of the specimen sample.

FIG. 19 illustrates a method for obtaining a specimen sample and storing the specimen sample, and method for transport and preservation of the specimen sample.

In step 100, the method begins. In step 101, a package is peeled apart and a collection swab is removed from a protective package. Proceed to step 102.

In step 102, the cap and the shaft are grasped and pulled back from the protective tube to remove a collection head from the protective tube. Proceed to step 103.

In step 103, the cap and plug are removed from the shaft of the collection swab. By removing the cap and plug, the useable of the length of the shaft of the collection swab can be maximized as well as to maintain a firm grip on the shaft. The cap and plug are removed from the shaft toward a first end of the shaft in a direction away from the collection head of the collection swab. Proceed to step 104.

In step 104, the collection head is swabbed against an inner cheek of the mouth of an animal to extract the buccal cell specimen for a predetermined period of time. The predetermined period of time should be long enough to scrape a sufficient amount of a cellular specimen from the inner cheek of the animal. The process proceeds to step 105.

In step 105, the cap and plug are replaced back onto the shaft, over and from the first end of the shaft, i.e., opposite the collection head along the shaft. The cap and plug are then slid back over the shaft to a predetermined position so that the collection head may be disposed comfortably within the protective tube as it is placed back into of the protective tube. The method then proceeds to step 106.

In step 106, the cap is aligned and inserted back securely into an open end of the protective tube until a flanged top portion of the cap seats flush with the open end of the protective tube. The process proceeds to step 107.

In step 107, the shaft of the collection swab is then pulled back out of the center of the cap, now seated within the protective tube, so that the collection head of the swab may be completely disengaged from a second end of the shaft. Likewise, the shaft is completely removed from the center of the cap and from the protective tube. The process then moves to step 108.

In step 108, the center of the cap is plugged by the tethered plug. The outer diameter of the plug is dimensioned to snugly fit within an inner diameter of the center of the cap so that a tight seal may be formed when the plug is secured flush within the center of the cap. The process proceeds to step 109.

In step 109, the follicle sample collection card is removed from an envelope. The follicle sample collection card may take a plurality of different configurations. Proceed to step 110.

In step 110, tweezers are removed from a storage package, and the process proceeds to step 111.

In step 111, a predetermined number of hairs are extracted by being pulled from the animal close to the base of their hair. The object is to extract the hair and the follicle together as a complete sample. The method then proceeds to step 112.

In step 112, a protective backing is removed from an adhesive strip disposed on the follicle sample collection card, and the process proceeds to step 113.

In step 113, the various hairs extracted from the animal are substantially aligned vertically oriented to the adhesive strip. The objective is to affix the various hairs to the adhesive strip of the follicle sample collection card in a vertical orientation so that the follicles are positioned to one side of the adhesive strip in order to provide sufficient protection to the hairs and hair follicles during storage and transport. Proceed to step 114.

In step 114, the follicle sample collection card is closed at the seam and placed securely back into the envelope, and the process then proceeds to step 115.

In step 115, a specimen storage enrollment card is filled out with pertinent identification information about the sample and the person preserving the specimen sample, and the process moves to step 116.

In step 116, the various items are placed into a return envelope for storage and/or mailing. That is, the protective tube along with the sealed and secured swab head, the follicle sample collection card with the hair samples, and the specimen storage enrollment card is placed into the larger return envelope. The process then proceeds to step 117.

In step 117, the various items are placed into a larger return envelope within a predetermined time period after the extraction of the hair and saliva swab sample on the collection head. Ideally, the various samples will be returned in by a delivery service as soon as possible to a storage facility to ensure maximum DNA integrity of the various samples. The process then proceeds to step 118.

In step 118, the storage facility (or laboratory or the like) receives the various genetic specimens. Once the genetic specimens are received at a storage facility, the buccal cells are transferred from the collection head of the swab onto a safe, secure and reliable medium for storage designed for the collection and control-temperature storage above freezing of biological samples for subsequent DNA analysis and use. Since the genetic material has sufficiently dried prior to arrival at the storage facility, a purified liquid or moistener, such as distilled, purified water or the like may be applied to the collection head 15 in order to transfer the buccal cells from the collection head to the storage medium. The storage facility may be provided at a control temperature above freezing and/or any suitable climate and humidity controlled environment in which the genetic specimen will be archived and preserved for sufficiently long periods of time, such as a couple of years to various decades. The process then proceeds to step 119.

In step 119, acknowledgment of receipt of the specimen by parcel delivery is received within another predetermined period of time after receipt and processing by the storage facility. Various suitable times for receipt of acknowledgment are possible, such as for example, 14 days after mailing of the sample in the return envelope. In step 120, the process ends.

Various advantages can be realized utilizing the kit for sampling, storing and transporting cellular specimens, and the method of preservation in accordance with this invention. The kit is inexpensive and easy to be used by inexperienced breeders. Breeders, not familiar with extracting DNA from a pet may readily do so in a simple and convenient manner. The breeder may now advantageously take DNA samples of all the animals in every litter. This way, if a breeder sells an animal that goes on to win a major award based on the animal's genetic make-up, the breeder would have that particular animal's DNA available in storage. Objectively, the breeder would be able to clone the prize winning animal and re-sell the animal again with the superior genetic DNA.

Other opportunities exist where a particular breeder could perform "time-shift breeding." That is, to take and store DNA samples for a number of years (e.g., 30 years) so that when the breeder decides to clone an animal they will have the option to pick any pairing of DNA (such as the genetically most desirable two) that they have ever had and breed them even though the two animals never co-existed because they were originally born a number of years apart (e.g. 15 or more years apart) and could have never been bred together, if not for having their DNA stored in accordance with the kit, systems and methods of this invention.

Breeders may be able to offer unique one of a kind cloning patterns with "no-clone" guarantees. That is, once the unique clone has been reproduced, that particular reproduced DNA can be retired and no longer reproduced. For example, once a unique clone has been made, the breeder could return any unused DNA to the owner of the clone, at the direction of the owner, destroy the unused portion or maintain the residual DNA through storage to support the unique one of a kind cloned animal. Likewise, where a naturally bred animal is provided to a new owner, the DNA for that animal may be turned over to the owner, and/or at the direction of the owner, the DNA can be destroyed, or stored exclusively for use by the owner of the naturally bred animal.

Other interesting schemes may be supported in accordance with the kit, systems and methods of this invention.

The breeders could also offer this as an incentive to buy since they would be buying the kits in bulk, they could sample/store the DNA for less than an individual with one pet. Something to distinguish them from their competition as every pet they sold had their DNA safely stored without the consumer having to worry about it.

It will be recognized by those skilled in the art that changes or modifications may be made to the above described embodiments without departing from the broad inventive concepts of the invention. Various other applications are possible in accordance with this invention. It is understood therefore that the invention is not limited to the particular embodiments which are described, but is intended to cover all modifications and changes within the scope and spirit of the invention.

What is claimed is:

1. A kit for collecting genetic sample of an animal, storing and transporting the genetic samples, comprising:
   a collection swab having a collection head and a shaft with
      a cap removably encircled around the shaft and a plug connected to the cap; and
   a protective tube adapted to receive the collection swab; or
   a follicle sample collection card having a protective backing covering an adhesive strip disposed on the follicle sample collection card; and
   an extraction device provided to pull at least one hair with follicle from the animal.

2. The kit for collecting genetic sample of an animal, storing and transporting the genetic samples as recited in claim 1, wherein the kit further comprises:
 a specimen storage enrollment card to record pertinent information; and
 an envelope for storage and delivery of the protective tube and the follicle sample collection card including the respective genetic samples to one or more storage facilities for processing and storage.

3. The kit for collecting genetic sample of an animal, storing and transporting the genetic samples as recited in claim 1, wherein the extraction device is tweezers.

4. The kit for collecting genetic sample of an animal, storing and transporting the genetic samples as recited in claim 1, wherein the collection swab:
 is housed within a sterile protective package;
 the shaft is connected at one end by the collection head;
  wherein the collection head is scraped against an inner cheek of the mouth of the animal to collect a first genetic sample on the collection head.

5. The kit for collecting genetic sample of an animal, storing and transporting the genetic samples as recited in claim 1, wherein the at least one hair extracted is aligned and fastened to the adhesive strip disposed on the follicle sample collection card so that the hair is fastened by the adhesive strip and the follicles are positioned to one side of the adhesive strip.

6. The kit for collecting genetic sample of an animal, storing and transporting the genetic samples as recited in claim 1, wherein the sample collection card has a billfold configuration with a fold seam disposed therein.

7. The kit for collecting genetic sample of an animal, storing and transporting the genetic samples as recited in claim 1, wherein the genetic samples are capable of being stored in a controlled temperature above freezing for an extended period of time.

8. A method for collecting, and storing genetic samples, comprising:
 pulling a cap connected to a cap and encircling a shaft of a collection swab back away from within a protective tube to remove a collection head from within a sterile compartment within the protective tube;
 scraping the collection head against an inner cheek of the mouth of an animal to receive a first specimen sample;
 inserting the shaft securely back into an open end of the protective tube until a flanged top portion of the cap seats flush with the open end of the protective tube;
 pulling the shaft of the collection swab back out of a center of the cap until the collection head is completely disengaged from a second end of the shaft, and plugging the center of the cap with a plug;
 pulling at least one hair with follicle from the animal; and
 removing a protective backing from an adhesive strip disposed on a follicle sample collection card, and aligning the at least one hair pulled onto the adhesive strip so that the follicles are positioned to one side of the adhesive strip; and then
 closing the follicle sample collection card at a seam over the hair and follicle for storage.

9. The method for collecting, and storing genetic samples as recited in claim 8, where in the plugging the center of the cap by a plug step, the outer diameter of the plug is dimensioned to snugly fit within an inner diameter of the center of the cap so that a tight seal may be formed when the plug is secured flush within the center of the cap.

10. The method for collecting, and storing genetic samples as recited in claim 8, wherein the aligning the predetermined number of hairs pulled from the animal to the adhesive strip on the follicle sample collection card is adapted to provide sufficient protection to the hair and hair follicles during storage.

11. The method for collecting, and storing genetic samples as recited in claim 8, wherein the genetic samples are stored at room temperature.

12. A method for collecting, storing and transporting genetic samples taken from an animal, comprising:
 (i.) peeling a protective package open to access a collection swab;
 (ii.) grasping and pulling a cap and a shaft of the collection swab back from within a protective tube to remove the collection head from the protective tube;
 (iii.) removing the cap and the plug connected to the cap from the shaft of the collection swab;
 (iv.) scraping the collection head against an inner cheek of the mouth of the animal for a predetermined period of time;
 (v.) replacing the cap and the connected plug back onto the shaft from the first end of the shaft opposite the collection head along the shaft to a predetermined position;
 (vi.) aligning and inserting the shaft securely back into an open end of the protective tube until a flanged top portion of the cap seats flush with the open end of the protective tube;
 (vii.) pulling the shaft of the collection swab back out of a center of the cap until the collection head is completely disengaged from a second end of the shaft;
 (viii.) plugging the center of the cap by the plug;
 (xi.) pulling a predetermined number of hairs and each of their respective follicles from the animal;
 (xii.) removing a protective backing from an adhesive strip disposed on a follicle sample collection card;
 (xii.) aligning the predetermined number of hairs pulled from the animal to the adhesive strip so that the follicles are positioned to one side of the adhesive strip; and
 (xiii.) closing the follicle sample collection card at a seam and placing the follicle sample collection card back into an envelope.

13. The method for collecting, storing and transporting genetic samples as recited in claim 12, further comprising the steps of:
 (ix.) removing the follicle sample collection card from the envelope;
 (x.) removing a tweezers from a storage package;
 (xiv.) filling out a specimen storage enrollment card with pertinent information;
 (xv.) placing the protective tube along with the sealed and secured collection head, the follicle sample collection card with hair samples, and the specimen storage enrollment card into the return envelope within a predetermined time period after the extraction of the hair samples and collection head;
 (xvi.) returning by delivery service to one or more storage facilities for processing and storage;
 (xvii.) at the storage facility, processing by transferring the genetic sample from the collection head onto a storage medium that is capable of storage at a controlled temperature above freezing for extended periods of time; and,
 (xviii.) receiving acknowledgment of receipt of the specimen after receipt and processing by the storage facility.

14. The method for collecting, storing and transporting genetic samples as recited in claim 12, wherein (iii.) removing the cap and plug from the shaft of the collection swab is removed from the shaft toward a first end of the shaft in a direction away from the collection head of the collection swab.

15. The method for collecting, storing and transporting genetic samples as recited in claim 12, wherein (viii.) plugging the center of the cap by the plug is removed from the shaft toward the first end of the shaft in a direction away from the collection head of the collection swab, and     wherein the outer diameter of the plug is dimensioned to snugly fit within an inner diameter of the center of the cap so that a tight seal may be formed when the plug is secured flush within the center of the cap.

16. The method for collecting, storing and transporting genetic samples as recited in claim 12, wherein (xii.) the aligning the predetermined number of hairs pulled from the animal to the adhesive strip on the follicle sample collection card is adapted to provide sufficient protection to the hairs and hair follicles during storage and transport.

\* \* \* \* \*